(12) United States Patent
Loescher et al.

(10) Patent No.: US 8,034,988 B2
(45) Date of Patent: Oct. 11, 2011

(54) PROCESS FOR THE ALKYLATION OF ISOBUTANE WITH DILUTE PROPYLENE

(75) Inventors: Mitchell E. Loescher, Houston, TX (US); William M. Cross, Jr., Seabrook, TX (US); Lawrence A. Smith, Jr., Pasadena, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 489 days.

(21) Appl. No.: 12/234,153

(22) Filed: Sep. 19, 2008

(65) Prior Publication Data

US 2010/0076241 A1 Mar. 25, 2010

(51) Int. Cl.
*C07C 2/62* (2006.01)

(52) U.S. Cl. ........ 585/331; 585/711; 585/717; 585/730; 585/731

(58) Field of Classification Search .................. 585/331, 585/711, 717, 730, 731
See application file for complete search history.

(56) References Cited

U.S. PATENT DOCUMENTS

| | | | |
|---|---|---|---|
| 2,381,041 A * | 8/1945 | De Jong | 585/300 |
| 2,762,853 A | 9/1956 | Jones et al. | |
| 2,859,260 A | 11/1958 | Stiles | |
| 3,013,092 A | 12/1961 | Watson et al. | |
| 3,544,652 A | 12/1970 | Van Dijk et al. | |
| 3,867,475 A | 2/1975 | Estes et al. | |
| 3,922,319 A | 11/1975 | Brockington | |
| 5,443,799 A | 8/1995 | Alexanyan et al. | |
| 6,774,275 B2 | 8/2004 | Smith, Jr. et al. | |

OTHER PUBLICATIONS

International Search Report and Written Opinion issued in International Application No. PCT/US2009/044359, dated Oct. 28, 2009, 10 pages.

* cited by examiner

*Primary Examiner* — Thuan Dinh Dang
(74) *Attorney, Agent, or Firm* — Osha • Liang LLP

(57) ABSTRACT

A process for alkylation of propylene, the process including: contacting a stream comprising propylene and propane with sulfuric acid in a first reaction zone under conditions to form propylene sulfate esters; contacting the propylene sulfate esters with isoparaffin and sulfuric acid in an alkylation reaction zone under conditions to react the propylene sulfate esters and the isoparaffin to form a reactor effluent comprising an acid phase and a hydrocarbon phase comprising unreacted isoparaffin and alkylate product; separating the hydrocarbon phase from the sulfuric acid; separating the hydrocarbon phase to form a fraction comprising unreacted isoparaffin and a fraction comprising the alkylate product.

26 Claims, 2 Drawing Sheets

PROCESS FOR THE ALKYLATION OF ISOBUTANE WITH DILUTE PROPYLENE

BACKGROUND OF DISCLOSURE

1. Field of the Disclosure

Embodiments disclosed herein relate generally to the alkylation of propylene with isobutane. More particularly, embodiments disclosed herein relate to a process for the alkylation of isobutane with a dilute propylene stream under conditions to promote the propylene alkylation reaction and to avoid excessive oligomerization or polymerization of propylene.

2. Background

Alkylation is the reaction of paraffins, usually isoparaffins, with an olefin in the presence of a strong acid which produces paraffins, e.g., of higher octane number than the starting materials and which boils in the range of gasolines. In petroleum refining, the alkylation reaction is generally the reaction of a $C_3$ to $C_5$ olefin with isobutane.

In refining alkylations, hydrofluoric or sulfuric acid catalysts are commonly used. For sulfuric acid catalyzed alkylation, low temperature or cold acid processes are favored, minimizing side reactions. In a typical process, the reaction is carried out in a reactor where the hydrocarbon reactants are dispersed into a continuous acid phase.

For example, U.S. Pat. No. 2,762,853 discloses an alkylation process including feeding isoparaffins, such as isobutane or isopentane and $C_2$-$C_5$ monoolefins to an alkylation reactor. The alkylation reaction is catalyzed with sulfuric acid in excess of 88 percent, preferably in excess of 96 percent. The alkylation products are then separated into gasoline range components and heavier alkylate products, among other finishing processes.

As another example, U.S. Pat. No. 2,859,260 discloses an alkylation process including reacting isoparaffins with olefins in the presence of a sulfuric acid catalyst. The reaction product is then separated to recover a hydrocarbon-rich phase and an acid-rich phase. The hydrocarbon-rich phase is further treated to remove catalyst esters from the hydrocarbon phase, among other downstream operations. Another example of a prior art alkylation process is disclosed in U.S. Pat. No. 3,013,092.

Whereas the above alkylation reactions may occur in a single reactor, Albright et al. disclose a two-step alkylation process in which butyl sulfates or butyl fluorides are formed in the first step and alkylate is produced in the second step. See, for example, "Alkylation of Isobutane with $C_4$ Olefins. 1. First-Step Reactions Using Sulfuric Acid Catalyst," Lyle F. Albright et al., Ind. Eng. Chem. Res. 1988, 27, 381-386 and "Alkylation of Isobutane with $C_4$ Olefins. 3. Two-Step Process Using Sulfuric Acid Catalyst," Lyle F. Albright et al., Ind. Eng. Chem. Res. 1988, 27, 391-397.

In a modern refinery, one of the gasoline blending components comes from the FCC unit. This FCC unit also produces mixed C4's (butenes/butanes) and mixed C3's (propylene/propane). These light gasses are not suitable as gasoline, so they must be converted into gasoline components or converted into other useful products. In the sulfuric acid alkylation process, as discussed above, C4 olefins (butenes) are reacted with isobutane to produce a mixture of C6 to C9 paraffins. Because the alkylation process produces branched paraffins, the resulting octane value of the product is good. The disadvantages of the process include high energy use, and the need to regenerate and recycle the sulfuric acid due to the buildup of heavy compounds that are soluble in the acid, commonly referred to as "acid soluble oils," or ASO.

Normally, in a refinery, very few of the C3 compounds from the FCC unit are fed to the alkylation unit. The primary reason is that the reactive propylene is very stable once absorbed in the acid and alkylates slowly. Thus, one problem with conventional sulfuric-acid-catalyzed alkylation using propylene is that the stable absorbed propylene reacts slowly with isobutane. As a result, the propylene tends to form heavy compounds which necessitate additional acid regeneration.

The most prevalent process for conversion of propylene is commonly referred to as "poly." In a poly unit, the propylene is oligomerized over solid phosphoric acid (SPA) catalyst to form C6 and C9 olefins. These heavier olefins can then be used in gasoline. The non-reactive propane is then sold as a separate fuel. The SPA catalyst life is short and as the reaction gives off heat, the reactor consists of tubes and must be water cooled. In addition, the catalyst is often difficult to remove from the reactor after it is spent, and must sometimes be drilled out due to polymer formation. While this is expensive and maintenance intensive, the refiner has few other economic alternatives for dealing with propylene.

As another alternative, propylene may be separated from propane by distillation and sold as a chemical product. This option is not available to all refiners, as some do not have a nearby customer for the propylene. Consequently, these "stranded" refiners have no choice but to convert the propylene into gasoline range components. The present invention is a new Accordingly, there exists a need for alternative processes to convert propylene into gasoline in a way that produces more gasoline than oligomerization in a poly unit.

SUMMARY OF THE DISCLOSURE

In one aspect, embodiments disclosed herein relate to a process for alkylation of propylene, the process including: contacting a stream comprising propylene and propane with sulfuric acid in a first reaction zone under conditions to form propylene sulfate esters; contacting the propylene sulfate esters with isoparaffin and sulfuric acid in an alkylation reaction zone under conditions to react the propylene sulfate esters and the isoparaffin to form a reactor effluent comprising an acid phase and a hydrocarbon phase comprising unreacted isoparaffin and alkylate product; separating the hydrocarbon phase from the sulfuric acid; separating the hydrocarbon phase to form a fraction comprising unreacted isoparaffin and a fraction comprising the alkylate product.

In another aspect, embodiments disclosed herein relate to a process for alkylation of propylene, the process including: contacting a stream comprising propylene and propane with sulfuric acid in a first reaction zone at a temperature in the range from $-28°$ C. to $7°$ C. ($-20°$ F. to $45°$ F.) to form propylene sulfate esters; separating the propane from the sulfuric acid and the propylene sulfate esters; contacting the propylene sulfate esters with isobutane and sulfuric acid in an alkylation reaction zone at a temperature in the range from $-7°$ C. to $38°$ C. ($20°$ F. to $100°$ F.) to react the propylene sulfate esters and the isobutane to form a reactor effluent comprising an acid phase and a hydrocarbon phase comprising unreacted isoparaffin and alkylate product; separating the hydrocarbon phase from the sulfuric acid; separating the hydrocarbon phase to form a fraction comprising unreacted isoparaffin and a fraction comprising the alkylate product.

Other aspects and advantages will be apparent from the following description and the appended claims.

DETAILED DESCRIPTION

In one aspect, embodiments disclosed herein relate to the alkylation of hydrocarbon feedstocks. More particularly, embodiments disclosed herein relate to a process for alkylation of propylene and an isoparaffin. More particularly, embodiments disclosed herein relate to a process for the alkylation of isobutane with a dilute propylene stream under conditions to promote propylene alkylation reaction and to avoid excessive oligomerization or polymerization of propylene.

Alkylation feedstocks used in embodiments disclosed herein include mixtures of propylene with various paraffins. For example, alkylation feedstocks may include $C_1$-$C_5$ paraffins, including n-alkanes and iso-alkanes. In certain embodiments, paraffins may include propane, $C_4$ alkanes (n-butane and isobutane), $C_5$ alkanes (n-pentane, neopentane, and isopentane), and mixtures thereof. In some embodiments, high purity isoparaffins, such as isobutane and/or isopentane, are used as the paraffin feed. The propylene feedstock, in some embodiments, may be a mixture of propylene and propane, such as a dilute propylene stream containing 1 wt. % to 90 wt. % propylene in propane.

Dilute propylene may be mixed with sulfuric acid at temperatures and sulfuric acid to propylene molar ratios where propylene will readily chemisorb into the acid phase forming propylene sulfate ester. Temperatures and acid ratios may be controlled to suppress oligomer formation while the chemisorption reaction proceeds. High-efficiency mixing is not required. In some embodiments, propane vapors may be removed from the acid/hydrocarbon mixture at this point.

The mixture of acid and propylene sulfate is then fed to an alkylation reactor, such as a high efficiency contacting device, along with isoparaffin and sulfuric acid. In the alkylation reactor, the propylene sulfate ester reacts with isoparaffin to form C7 and/or C8 alkylate. Heavies formation may also be suppressed by keeping the amount of free propylene low during the alkylation reaction.

Following the above contacting, acid is separated for recycle to the contactor and the cold mixer. The hydrocarbon phase then enters a separation section where propane, if not previously separated, isobutane and alkylate are recovered. In some embodiments, such as where a high purity isobutane feed is used, very little n-butane will be present, and the separation section will be less expensive than typical for C4 alkylation units, which have to separate n-butane from isobutane.

As described above, by careful selection of mixing, contacting, and temperatures, the processes disclosed herein can efficiently alkylate propylene and isoparaffins, such as isobutane and isopentane, with minimal heavies formation.

Figure 1:
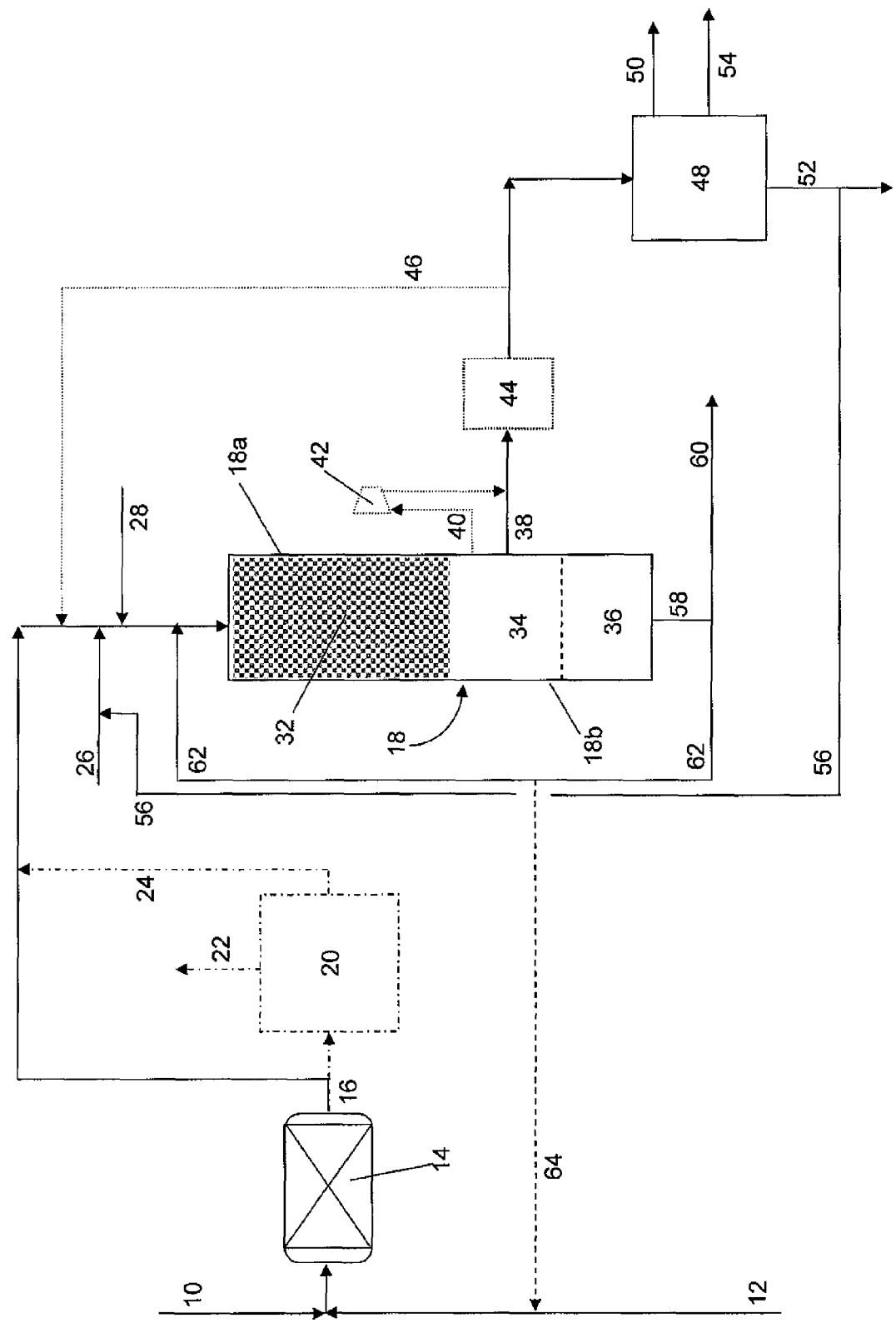
FIG. 1 is a simplified process flow diagram of a process for the alkylation of propylene according to embodiments disclosed herein.

Referring now to FIG. 1, a simplified process flow diagram of a process for alkylation of propylene, according to embodiments disclosed herein, is illustrated. Dilute propylene feedstock 10, which may include propylene and propane, may be contacted with a stream 12, which may include fresh or spent sulfuric acid, in a reactor 14. The contacting results in the formation of a mixed hydrocarbon/acid system.

Conditions in reactor 14 may be maintained such that at least a portion of the propylene reacts with the sulfuric acid to form propylene sulfate esters, as mentioned above, while minimizing formation of heavies. For example, in some embodiments, the temperature in reactor 14 may be maintained in the range from −29° C. to 7° C. (−20° F. to 45° F.); embodiments having other reactor conditions will be described below. At these conditions, the chemisorption of propylene into the acid phase and formation of propylene sulfate esters readily occurs in reactor 14. As intimate contact of the acid and propylene is not required, contact of the acid and dilute propylene may occur in any type of device to contact or mix feed streams, including piping, static mixers, agitated vessels, counter-current contact vessels, and co-current reactors or vessels including contact structures to promote the contact of the acid and hydrocarbon phases.

In some embodiments, the resulting reaction mixture 16, including propane and propylene sulfate esters, may be fed directly to an alkylation reactor 18 to react the propylene sulfate esters with an isoparaffin. In other embodiments, reaction mixture 16 may be separated, for example, by decanting the reaction mixture to recover a hydrocarbon fraction 22, including propane and any unreacted propylene, and an acid propylene sulfate ester fraction 24. As illustrated, where contact of propylene and acid are co-current in reactor 14, propane vapors may be separated from the acid sulfate ester using a separator 20, which may be a flash vessel, coalescer, decanter, or other types of separators that may be used to separate vapor/liquid mixtures or hydrocarbon/acid mixtures, as each may be used, or mixtures thereof. (Although not illustrated in FIG. 1, where contact of the propylene and acid are counter-current, propane may be recovered, for example, from the top of reactor 14 and the acid propylene sulfate ester fraction may be recovered from the bottom of reactor 14.)

Acid propylene sulfate ester fraction 16 (or 24) may then be contacted with isoparaffin fed via flow line 26 and a stream 28, which may include fresh or spent sulfuric acid, in alkylation reactor 18. Alkylation reactor 18 may include an upper section 18a and a bottom section 18b. Contact structures 32 may be positioned in upper section 18a to facilitate the intimate contact of the propylene sulfate esters, the isoparaffin, and the sulfuric acid.

Conditions in alkylation reactor 18 may be maintained such that at least a portion of the propylene sulfate ester reacts with the isoparaffin to form alkylate. The reaction mixture may then be separated, for example, by decanting the reaction mixture in lower section 18b to recover a hydrocarbon fraction 34, including alkylate, unreacted isoparaffin, and propane, when present, and an acid fraction 36.

Hydrocarbon fraction 34 may be recovered from alkylation reactor 18 via line 38. Additionally, the heat of reaction may produce some vapors, which may be removed via line 40. If desired, these vapors may be condensed or compressed, such as by using a compressor 42, and combined with the hydrocarbons in line 38.

If desired, the recovered hydrocarbons in line 38 may pass through a de-entrainment device 44. Additionally, a portion of the recovered hydrocarbon fraction may be recycled via line 46 to the top of reactor 18, such as for purposes of reactor temperature control and to react any unreacted isoparaffin recovered via line 38.

The remaining hydrocarbons, including isoparaffin, alkylate, unreacted propylene, and propane, where a separator 20 is not used, may be separated into product streams via a separation unit 48. Separation unit 48, in some embodiments, may include one or more distillation columns for example, and may be used to recover a propane fraction 50 (if necessary), an isoparaffin fraction 52, and an alkylate product stream 54. In some embodiments, isoparaffin fraction 52 may be recycled to alkylation reactor 18 via flow line 56.

Acid fraction 36, which may include unreacted propylene sulfate esters and sulfuric acid, may be recovered from alkylation reactor 18 via line 58. At least a portion of the recovered acid fraction in line 58 may be purged via line 60. In some embodiments, a portion of the acid fraction recovered via line 58 may also be recycled via line 62, such as to maintain a desired acid concentration in reactor 18a. In other embodiments, a portion of the recovered acid may fed via flow line 64 as a spent acid feed to the sulfate ester reactor 14.

Figure 2:
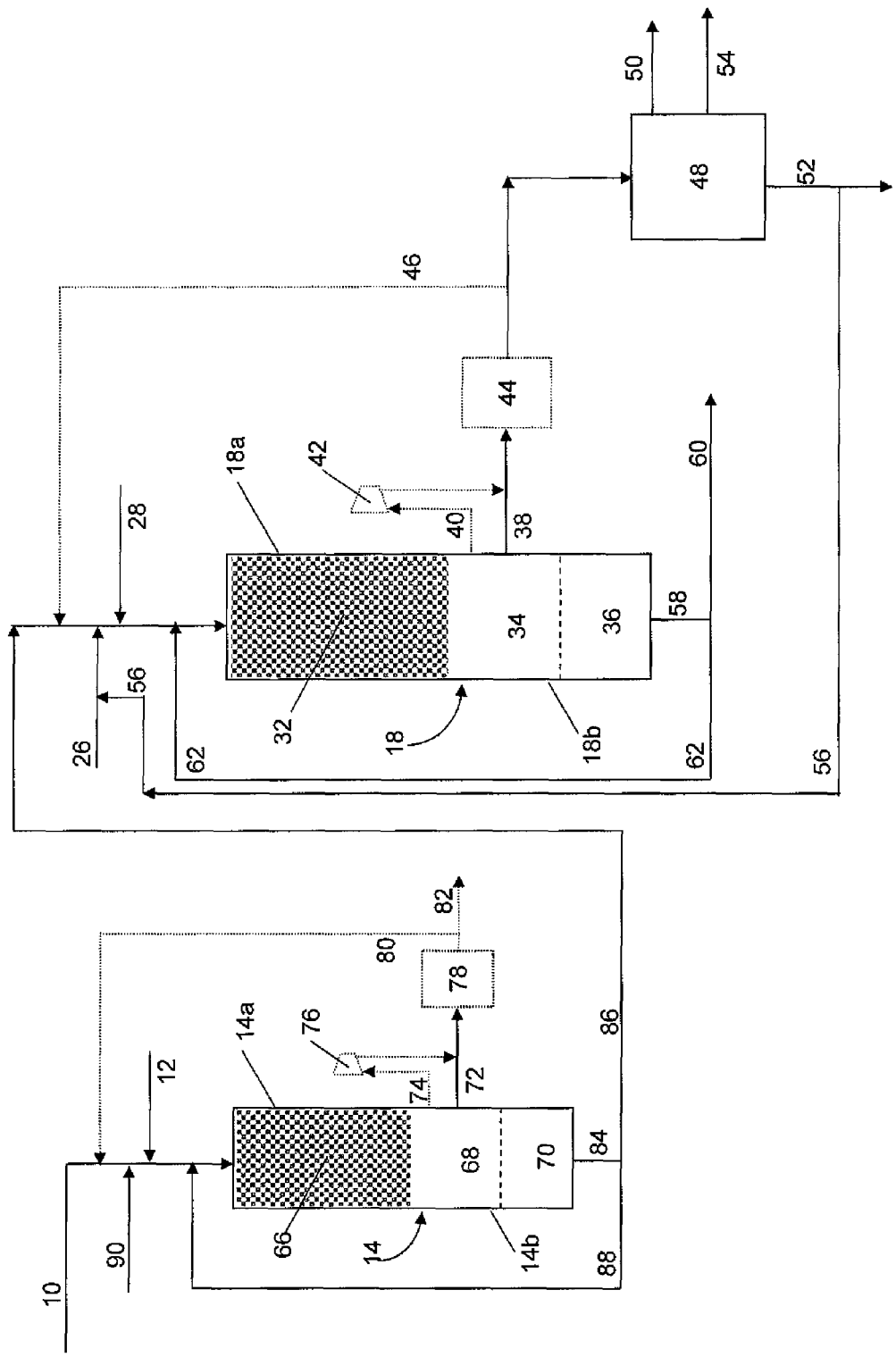
FIG. 2 is a simplified process flow diagram of a process for the alkylation of propylene according to embodiments disclosed herein.

A reactor that may be used for the reaction of propylene with sulfuric acid to form propylene sulfate esters, in some embodiments, may include a scaled down version of an alkylation reactor, such as reactor 18 illustrated in FIG. 1. Use of such a reactor is illustrated in FIG. 2, where like numerals represent like parts. Referring to FIG. 2, a simplified process flow diagram of a process for alkylation of propylene, according to embodiments disclosed herein, is illustrated. Dilute propylene feedstock 10, which may include propylene and propane, may be contacted with a stream 12, which may include fresh or spent sulfuric acid, in a reactor 14. The contacting results in the formation of a mixed hydrocarbon/acid system.

Reactor 14 may be similar to an alkylation reactor, and may include an upper section 14a and a bottom section 14b. Contact structures 62 may be positioned in upper section 14a to facilitate the contact of the olefins with the sulfuric acid. Conditions in reactor 14 may be maintained such that at least a portion of the propylene reacts with the sulfuric acid to form propylene sulfate esters. The reaction mixture may then be separated, for example, by decanting the reaction mixture in lower section 14b to recover a hydrocarbon fraction 68, including propane and any unreacted propylene, and an acid propylene sulfate ester fraction 70.

Hydrocarbon fraction 68 may be recovered via line 72. Additionally, the heat of reaction may produce some vapors, which may be removed via line 74. If desired, these vapors may be condensed or compressed, such as by using a compressor 76, and combined with the hydrocarbons in line 72.

If desired, the recovered hydrocarbons may pass through a de-entrainment device 78. Additionally, a portion of the recovered hydrocarbon fraction may be recycled via line 80 to the top of reactor 14, such as for purposes of reactor temperature control and to react any unreacted propylene recovered via line 72.

Acid propylene sulfate ester fraction 70, which may include propylene sulfate esters and excess sulfuric acid, may be recovered via line 84. At least a portion of the recovered acid sulfate ester fraction may be forwarded as alkylation feed to an alkylation unit, similar to that described with respect to FIG. 1, via line 86. A portion of acid sulfate ester fraction 70 recovered via line 84 may also be recycled via line 88, such as to maintain a desired acid concentration in reactor 14a.

Stream 12 may include spent sulfuric acid from a cold acid alkylation unit in some embodiments. In other embodiments, stream 12 may include fresh sulfuric acid at an appropriate concentration. In yet other embodiments, additional olefins, such as butenes, pentenes, and mixtures thereof, may be added to reactor 14a via line 90, resulting in additional sulfate esters for use in downstream alkylation processes.

In some embodiments, a pulse flow regime may be used for the sulfate ester and/or alkylation reactions. The pulses may be characterized by large mass and heat transfer rates. Increased contact structure wetting and a continuous mixing between parallel flowing rivulets may diminish flow maldistribution. In addition, the formation of local hot spots may be reduced, leading to an intrinsically safer process. The pulses may continuously mobilize stagnant liquid holdup to the point where its stagnant nature disappears. Since stagnant holdup represents 10 to 30 percent of the total liquid holdup in trickle flow operations, the dynamic character of the pulse flow regime may enhance reactor performance, such as by improved radial mixing.

As described above, contact structures may be positioned in the sulfate ester and alkylation reactors for contacting the sulfuric acid and a feed stream comprising n-olefins. In some embodiments, contact structures or dispersers used in embodiments described herein may include at least 50 percent void space; at least 60 percent void space in other embodiments; at least 70 percent void space in other embodiments; at least 80 percent void space in other embodiments; and up to 99 percent void space in yet other embodiments. For example, in some embodiments, a contact structure may include a multi-filament component and a structural element, such as a co-knit wire mesh, dispersers, or other suitable contact structures. For example, contact structures as described in U.S. Pat. No. 6,774,275, incorporated herein by reference, may be used.

Reaction of olefins and sulfuric acid to form sulfate ester, as described above, is performed at conditions to preferentially form sulfate esters and to avoid heavies formation (oligomerization or polymerization of the feed), allowing for the separation of the propane prior to alkylation. The sulfate ester reactor operating conditions may include reaction temperatures ranging from −34 to 43° C. (−30 to 110° F.) in some embodiments; ranging from −29 to 7° C. (−20 to 45° F.) in other embodiments; ranging from −23 to 4° C. (−10 to 40° F.) in other embodiments; and ranging from −18 to 2° C. (0 to 35° F.) in yet other embodiments. Reactor pressures may range from about 5 to about 500 psig in some embodiments; from about 10 to 250 psig in other embodiments; and from about 20 to 150 psig in yet other embodiments. The combination of temperature and pressure used in some embodiments is sufficient to maintain the feed and products in the liquid phase.

In some embodiments, the concentration of sulfuric acid phase entering the sulfate ester reactor may be maintained at a concentration that titrates as below 75 weight percent strength sulfuric acid/water mixtures or less. In other embodiments, the sulfuric acid may be maintained at a concentration range titrating as 20 to 50 weight percent sulfuric acid/water mixtures; titrating as 25 to 45 weight percent sulfuric acid/water mixtures in other embodiments; and titrating as 30 to 40 weight percent sulfuric acid/water mixtures in yet other embodiments. It can be noted that that the acid phase entering the sulfate ester reactor in these instances is composed of sulfuric acid, ASO (acid soluble oils) and water. It does not contain significant quantities of water, typically 0-5% by weight, and for the purposes of describing the acid content, the terminology "titrates as" or "titrating as" is used to indicate a sulfuric acid/water mixture which has the same acidity, understanding that the acid mixture used herein is more complex in chemical makeup. Measurement of the acidity may be measured, for example, using a METTLER DL-77 or a METTLER T-90 titrator.

The formation of the propylene sulfate esters may be performed where sulfuric acid is present in at least a stoichiometric ratio to the propylene in the reactor feed. In other embodiments, sulfuric acid may be present in a range from about 0.9 to about 4 times the stoichiometric ratio; from about 1 to about 3 times the stoichiometric ratio in other embodiments; and from about 1 to about 2 times the stoichiometric ratio in yet other embodiments.

Conditions in the alkylation reactor to form alkylate product from propylene and isoparaffin are also controlled so as to avoid formation of heavies. Alkylation reactor operating conditions may include reaction temperatures ranging from −7 to 38° C. (20 to 100° F.) in some embodiments; ranging from −4 to 18° C. (25 to 65° F.) in other embodiments; ranging from −1 to 10° C. (30 to 50° F.) in other embodiments; and ranging from −7 to 4° C. (20 to 40° F.) in yet other embodiments. Reactor pressures may range from about 5 to about 500 psig in some embodiments; from about 10 to 250 psig in other embodiments; and from about 20 to 150 psig in yet other embodiments. The combination of temperature and pressure used in some embodiments is sufficient to maintain the feed and products in the liquid phase. Under such conditions, the propylene sulfate reacts with isobutane and isopentane to form C7 and C8 alkylate. Heavies formation is also suppressed as the amount of free propylene is kept low during the alkylation reaction.

Sulfuric acid fed to the alkylation reactor may include fresh or recycled sulfuric acid. In some embodiments, the concentration of sulfuric acid phase entering the alkylation reactor may be maintained at a concentration that titrates as below 98 weight percent strength sulfuric acid/water mixtures or less. In other embodiments, the sulfuric acid may be maintained at a concentration range titrating as 20 to 80 weight percent sulfuric acid/water mixtures; titrating as 25 to 75 weight percent sulfuric acid/water mixtures in other embodiments; and titrating as 30 to 70 weight percent sulfuric acid/water mixtures in yet other embodiments. It can be noted that that the acid phase in these instances is composed of sulfuric acid, sulfate esters, ASO (acid soluble oils) and water. It does not contain significant quantities of water, typically 0-5% by weight, and for the purposes of describing the acid content, the terminology "titrates as" or "titrating as" is used to indicate a sulfuric acid/water mixture which has the same acidity, understanding that the acid mixture used herein is more complex in chemical makeup. Measurement of the acidity may be measured, for example, using a METTLER DL-77 or a METTLER T-90 titrator.

In some embodiments, a mass ratio of the sulfuric acid to the propylene sulfate ester fed to the alkylation reaction zone is in the range from 0.5:1 to 30:1. In other embodiments, a mass ratio of the sulfuric acid to the propylene sulfate ester fed to the alkylation reaction zone is in the range from 0.9:1 to 20:1; and in the range from 1:1 to 10:1 in yet other embodiments.

In some embodiments, a mass ratio of the isoparaffin to the propylene sulfate ester fed to the alkylation reaction zone is in the range from 0.5:1 to 30:1. In other embodiments, a mass ratio of the sulfuric acid to the propylene sulfate ester fed to the alkylation reaction zone is in the range from 0.9:1 to 25:1; and in the range from 1:1 to 20:1 in yet other embodiments.

The C7 and C8 alkylate formed using embodiments of the processes disclosed herein may be used as gasoline. In some embodiments, the C7 and C8 alkylate products may be blended with other components to form a gasoline.

As described above, by careful selection of the reactor temperatures, mixing conditions, acid to propylene ratios, and isoparaffin to propylene sulfate ester ratios, processes disclosed herein may alkylate isoparaffins, such as isobutane and isopentane, with propylene. Advantageously, embodiments disclosed herein may allow for formation of C7 and C8 gasoline pool products from propylene, with minimal formation of heavies, such as due to oligomerization and polymerization. Additionally, processes disclosed herein may provide alternatives that may be especially useful for "stranded" refiners to form gasoline range products, thus avoiding expensive and maintenance intensive processes, such as propylene oligomerization. Further, embodiments disclosed herein may provide a beneficial use for spent sulfuric acid.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for alkylation of propylene, the process comprising:

contacting a stream comprising propylene and propane with sulfuric acid in a first reaction zone under conditions to form propylene sulfate esters;

contacting the propylene sulfate esters with isoparaffin and sulfuric acid in an alkylation reaction zone under conditions to react the propylene sulfate esters and the isoparaffin to form a reactor effluent comprising an acid phase and a hydrocarbon phase comprising unreacted isoparaffin and alkylate product;

separating the hydrocarbon phase from the sulfuric acid;

separating the hydrocarbon phase to form a fraction comprising unreacted isoparaffin and a fraction comprising the alkylate product;

wherein a molar ratio of the sulfuric acid to the propylene fed to the first reaction zone is in the range from 1:1 to 3:1; and wherein the sulfuric acid fed to the first reaction zone has a strength that titrates as less than 75 weight percent $H_2SO_4$/water mixtures.

2. The process of claim 1, wherein the stream comprising propylene and propane comprises from 1 to 90 weight percent propylene.

3. The process of claim 1, further comprising separating the propane from the propylene sulfate esters prior to the contacting the propylene sulfate esters with isoparaffin.

4. The process of claim 1, wherein the hydrocarbon phase further comprises propane, the separating the hydrocarbon phase further comprising forming a fraction comprising propane.

5. The process of claim 1, further comprising recycling at least a portion of the sulfuric acid separated from the hydrocarbon phase to the first reaction zone.

6. The process of claim 1, further comprising recycling at least a portion of the fraction comprising isoparaffin to the alkylation reaction zone.

7. The process of claim 1, wherein the contacting in the first reaction zone is at a temperature in the range from −28° C. to 7° C. (−20° F. to 45° F.).

8. The process of claim 1, wherein the contacting in the alkylation reaction zone is at a temperature in the range from −7° C. to 38° C. (20° F. to 100° F.).

9. The process of claim 1, wherein a mass ratio of the sulfuric acid to the propylene sulfate ester fed to the alkylation reaction zone is in the range from 1:1 to 10:1.

10. The process of claim 1, wherein a mass ratio of the isoparaffin to the propylene sulfate ester fed to the alkylation reaction zone is in the range from 1:1 to 20:1.

11. The process of claim 1, wherein the isoparaffin comprises at least one of isobutane, isopentane, and mixtures thereof.

12. The process of claim 11, wherein the isoparaffin comprises isobutane.

13. The process of claim 1, further comprising feeding at least one of butene and pentene to the first reaction zone.

14. The process of claim 1, wherein the sulfuric acid fed to the first reaction zone has a strength that titrates in the range from 20 to 50 weight percent $H_2SO_4$/water mixtures.

15. The process of claim 1, wherein the sulfuric acid fed to the first reaction zone has a strength that titrates in the range from 30 to 40 weight percent $H_2SO_4$/water mixtures.

16. A process for alkylation of propylene, the process comprising:
- contacting a stream comprising propylene and propane with sulfuric acid in a first reaction zone at a temperature in the range from −28° C. to 7° C. (−20° F. to 45° F.) to form propylene sulfate esters;
- separating the propane from the sulfuric acid and the propylene sulfate esters;
- contacting the propylene sulfate esters with isobutane and sulfuric acid in an alkylation reaction zone at a temperature in the range from −7° C. to 38° C. (20° F. to 100° F.) to react the propylene sulfate esters and the isobutane to form a reactor effluent comprising an acid phase and a hydrocarbon phase comprising unreacted isoparaffin and alkylate product;
- separating the hydrocarbon phase from the sulfuric acid;
- separating the hydrocarbon phase to form a fraction comprising unreacted isoparaffin and a fraction comprising the alkylate product;
- wherein a molar ratio of the sulfuric acid to the propylene fed to the first reaction zone is in the range from 1:1 to 3:1; and
- wherein the sulfuric acid fed to the first reaction zone has a strength that titrates as less than 75 weight percent $H_2SO_4$/water mixtures.

17. The process of claim 16, wherein the separating the propane comprises decanting.

18. The process of claim 16, wherein the separating the hydrocarbon phase from the sulfuric acid comprises decanting.

19. The process of claim 16, wherein the stream comprising propylene and propane comprises from 1 to 90 weight percent propylene.

20. The process of claim 16, further comprising recycling at least a portion of the sulfuric acid separated from the hydrocarbon phase to the first reaction zone.

21. The process of claim 16, further comprising recycling at least a portion of the fraction comprising isoparaffin to the alkylation reaction zone.

22. The process of claim 16, wherein a mass ratio of the sulfuric acid to the propylene sulfate ester fed to the alkylation reaction zone is in the range from 1:1 to 10:1.

23. The process of claim 16, wherein a mass ratio of the isoparaffin to the propylene sulfate ester fed to the alkylation reaction zone is in the range from 1:1 to 20:1.

24. The process of claim 16, further comprising feeding at least one of butene and pentene to the first reaction zone.

25. The process of claim 16, wherein the sulfuric acid fed to the first reaction zone has a strength that titrates in the range from 20 to 50 weight percent $H_2SO_4$/water mixtures.

26. The process of claim 16, wherein the sulfuric acid fed to the first reaction zone has a strength that titrates in the range from 30 to 40 weight percent $H_2SO_4$/water mixtures.

* * * * *